United States Patent [19]

Shoji et al.

[11] Patent Number: 5,693,806
[45] Date of Patent: Dec. 2, 1997

[54] PROCESS FOR PRODUCING PYRAZINE COMPOUNDS

[75] Inventors: Takayuki Shoji; Toru Nakaishi, both of Osaka; Masafumi Mikata, Nishinomiya, all of Japan

[73] Assignee: Koei Chemical Co., Ltd., Osaka, Japan

[21] Appl. No.: 681,475

[22] Filed: Jul. 23, 1996

[30] Foreign Application Priority Data

Aug. 4, 1995 [JP] Japan .................................. 7-219857

[51] Int. Cl.$^6$ .................................................. C07D 241/02
[52] U.S. Cl. ............................................................ 544/410
[58] Field of Search ............................................... 544/410

[56] References Cited

U.S. PATENT DOCUMENTS 4,097,478  6/1978  Sato ........................................ 544/353

FOREIGN PATENT DOCUMENTS 54-132588  10/1979  Japan .
8-224473   9/1996   Japan .

*Primary Examiner*—Mukund J. Shah
*Assistant Examiner*—Brenda Coleman
*Attorney, Agent, or Firm*—Birch, Stewart, Kolasch & Birch, LLP

[57] ABSTRACT

A process for producing a pyrazine compound of the general formula (3):

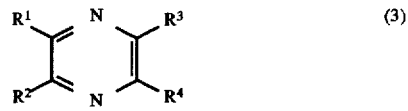

wherein $R^1$, $R^2$, $R^3$ and $R^4$ represent a hydrogen atom or a lower alkyl group, which comprises catalytically reacting in a gaseous phase a diamine compound of the general formula:

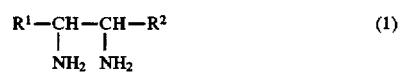

with a diol compound of the general formula:

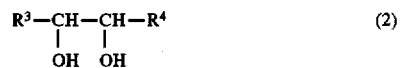

in the presence of a catalyst containing hydrogen-treated silver or a catalyst containing silver and at least one element selected from the group consisting of alkali metals, alkaline earth metals, zinc and lanthanoid elements.

6 Claims, No Drawings

5,693,806

PROCESS FOR PRODUCING PYRAZINE COMPOUNDS

BACKGROUND OF THE INVENTION

1. Field of the Invention

The present invention relates to a process for producing a pyrazine compound by catalytically reacting a diamine compound with a diol compound in a gaseous phase.

Said pyrazine compound is useful as an intermediate for perfumes, pharmaceutical chemicals and agricultural chemicals.

2. Background Information

JP-A-54-132588 discloses, as an example of processes for producing a pyrazine compound by catalytically reacting a diamine compound with a diol compound in a gaseous phase, a process for producing 2-methylpyrazine by catalytically reacting ethylene diamine with propylene glycol in a gaseous phase in the presence of a catalyst mainly consisting of zinc oxide. This process, however, is not satisfactory as a process for industrial production of pyrazines because the process requires a high reaction temperature such as 470°–480° C. and the utmost yield of the 2-methylpyrazine at said reaction temperature is 64%.

The purpose of the present invention is to provide a process which allows production of pyrazine compounds at a relatively low reaction temperature and in a high yield, using diamine compounds and diol compounds as the starting materials.

As the result of extensive research, the present inventors have found that pyrazine compounds may be produced at a relatively low reaction temperature and in a high yield when a diamine compound and a diol compound are catalytically reacted in a gaseous phase in the presence of a catalyst containing hydrogen-treated silver. Thus the present invention was completed. Further, the present inventors have found that pyrazine compounds may be produced at a relatively low reaction temperature and in a high yield when a diamine compound and a diol compound are catalytically reacted in a gaseous phase in the presence of a catalyst containing silver not treated with hydrogen and at least one element selected from the group consisting of alkali metals, alkaline earth metals, zinc and lanthanoid elements.

SUMMARY OF THE INVENTION

Accordingly, the present invention relates to a process for producing a pyrazine compound (hereinafter, referred to as the pyrazine compound (3)) of the formula (3):

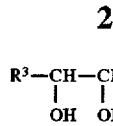

wherein $R^1$, $R^2$, $R^3$ and $R^4$, which are the same or different from each other, represent a hydrogen atom or a lower alkyl group, which comprises catalytically reacting in a gaseous phase a diamine compound (hereinafter, referred to as the diamine compound (1)) of the formula (1):

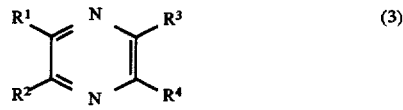

wherein $R^1$ and $R^2$ are the same as defined above, with a diol compound (hereinafter, referred to as the diol compound (2)) of the formula (2):

wherein $R^3$ and $R^4$ are the same as defined above, in the presence of a catalyst containing hydrogen-treated silver.

The present invention also relates to a process for producing the pyrazine compound (3) which comprises catalytically reacting in a gaseous phase the diamine compound (1) and the diol compound (2) in the presence of a catalyst containing silver and at least one element selected from the group consisting of alkali metals, alkaline earth metals, zinc and lanthanoid elements.

DETAILED DESCRIPTION OF THE INVENTION

The process for producing the pyrazine compound (3) according to the present invention is described below in more detail.

In the diamine compound (1) used in the present invention, $R^1$ and $R^2$ as substituents are the same or different from each other and represent a hydrogen atom or a lower alkyl group. Examples of the lower alkyl group include an alkyl group having 1 to 4 carbon atoms and specifically a methyl group, an ethyl group, an n-propyl group, an isopropyl group, an n-butyl group, an isobutyl group, a sec-butyl group and a tert-butyl group. Specific examples of the diamine compound (1)include, without limitation, ethylene diamine, 1,2-diaminopropane, 1,2-diaminobutane and 2,3-diaminobutane.

In the diol compound (2), $R^3$ and $R^4$ are the same or different from each other and represent a hydrogen atom or a lower alkyl group. Examples of the lower alkyl group include the same group as described for $R^1$ and $R^2$ in the diamine compound (1). Specific examples of the diol compound (2) include, without limitation, ethylene glycol, propylene glycol, 1,2-butanediol, 2,3-butanediol, 1,2-pentanediol, 2,3-pentanediol, 1,2-hexanediol and 3,3-dimethyl-1,2-butanediol.

Examples of the pyrazine compound (3) produced by the process of the present invention include, without limitation, pyrazine, 2-methylpyrazine, 2-ethylpyrazine, 2-propylpyrazine, 2-butylpyrazine, 2,3-dimethylpyrazine, 2,5-dimethylpyrazine, 2,6-dimethylpyrazine, 2,3,5-trimethylpyrazine, 2,3-dimethyl-5-ethylpyrazine and 2,3,5,6-tetramethylpyrazine.

In the present invention, when the diamine compound (1) is catalytically reacted with the diol compound (2) in a gaseous phase, a catalyst containing hydrogen-treated silver catalyst (hereinafter, referred to as the silver catalyst (a)) or a catalyst containing silver, which may not be a hydrogen-treated one, and at least one element selected from the group consisting of alkali metals, alkaline earth metals, zinc and lanthanoid elements (hereinafter, referred to as the silver catalyst (b)) is used.

The silver catalyst (a) is not particularly limited insofar as it contains the hydrogen-treated silver as the active ingredient.

In the silver catalyst (a) in the present invention, the hydrogen-treated silver is usually carried on a carrier. The carrier is, usually, at least one selected from the group consisting of alumina, zirconia and silicon carbide, and is preferably alumina or zirconia.

When the silver catalyst (a) in the present invention is one having hydrogen-treated silver supported on a carrier, the amount of the hydrogen-treated silver is not particularly limited and is usually 1–50% by weight, preferably 2–30% by weight, of the catalyst.

The silver catalyst (a) used in the present invention is sufficiently active even if it comprises the hydrogen-treated silver alone. When, however, the silver catalyst (a) comprises, as an additional constitutive element, at least one element selected from the group consisting of alkali metals, alkaline earth metals, zinc and lanthanoid elements, the yield of the pyrazine (3) increases. Moreover, when the silver catalyst (a) is a catalyst in which the hydrogen-treated silver and said additional constitutive element are supported on a carrier, preferably on alumina or zirconia, the yield of the pyrazine (3) further increases. When the silver catalyst (a) in the present invention comprises said additional constitutive element, said additional constitutive element is preferably comprised in the form of an oxide.

When the silver catalyst (a) in the present invention is a catalyst in which the hydrogen-treated silver and said additional constitutive element are supported on a carrier, the amount of the additional constitutive element is not particularly limited and is usually 0.01–10% by weight, preferably 0.1–5% by weight of the catalyst when said constitutive element is an alkali metal, an alkaline earth metal or a lanthanoid element, or 0.5–20% by weight, preferably 1–15% by weight of the catalyst when said additional constitutive element is zinc.

The silver catalyst (a) in the present invention can be obtained by treating a catalyst containing at least silver (hereinafter, referred to as the silver catalyst (c)) with hydrogen. The silver catalyst (c) may comprise the above-mentioned additional constitutive element in the silver catalyst (a). That is, the silver catalyst (b) is an example of the silver catalyst (c). The raw material for silver or said additional constitutive element used for preparing the silver catalyst (c) includes metals and compounds containing the element, such as those exemplified below. The compounds containing the element are not particularly limited and may be any compounds conventionally used for the preparation of catalysts.

Examples of silver compounds include silver nitrate and silver chloride. Examples of compounds of alkali metals or alkaline earth metals include chlorides, hydroxides, nitrates and sulfates of lithium, sodium, potassium, cesium, rubidium, magnesium, calcium or barium. Examples of the zinc compounds include oxide, nitrate and sulfate of zinc. Examples of the lanthanoid compounds include chlorides, hydroxides, nitrates and sulfates of lanthanum, cerium, neodymium or samarium.

The silver catalyst (c) can be produced by processes generally known to the man skilled in the art for preparing catalysts. When, in the silver catalyst (c), at least silver is supported on at least one carrier selected from the group consisting of alumina, zirconia and silicon carbide, the silver catalyst (c) can be prepared, for example, by a process in which a powdery carrier is added in a liquid containing a raw material compound of silver and optionally a raw material compound of the additional constitutive element, and the obtained mixture is concentrated, dried and calcined, a process in which a carrier is dipped in said liquid, and the obtained carrier having at least silver compound is dried and calcined or the like.

The hydrogen treatment of the silver catalyst (c) obtained in this way can be effected, for example, by charging the silver catalyst (c) in a reactor and contacting a hydrogen-treating agent fed optionally with a diluent with the silver catalyst (c) charged portion of the reactor. As the hydrogen-treating agent, hydrogen or a compound capable of generating hydrogen may be used. The compound capable of generating hydrogen refers to a compound which can be decomposed, generating hydrogen upon contact with the silver catalyst (c). Any such compound can be used and examples include, without limitation, formaldehyde. Preferred examples of the diluent include inert gases such as steam and nitrogen.

The temperature for treating the silver catalyst (c) with hydrogen is not particularly limited and is usually 250°–450° C., preferably 300°–400° C. When hydrogen is used as the hydrogen-treating agent, the rate of feeding the hydrogen-treating agent is usually 0.1–10 ml/minute, preferably 0.3–5 ml/minute, per 1 ml of the silver catalyst (c). When formaldehyde is used as the hydrogen-treating agent, formaldehyde is fed in such a manner that the amount of generating hydrogen is the same as that of hydrogen when used, since 1 mole of formaldehyde generates 1 mole of hydrogen. When the diluent is used, the amount of the diluent is not particularly limited and is usually 0.1–10 moles, preferably 0.2–8 moles, per 1 mole of the hydrogen-treating agent. Upon feeding of the hydrogen-treating agent into the reactor, the hydrogen treatment of the silver catalyst (c) proceeds with generation of heat observed in the silver catalyst (c) charged area, and said generation of heat is not observed after completion of the hydrogen-treatment. Therefore, the end point of the hydrogen-treatment is the time at which the generation of heat in the silver catalyst (c) charged area ceases but usually feeding of the hydrogen-treating agent is continued for an additional several minutes.

The production of the pyrazine compound (3) according to the present invention can be performed usually by feeding a mixed gas of the diamine compound (1) and the diol compound (2) into a reactor in which the silver catalyst (a) or the silver catalyst (b) is packed. The mixed gas may be fed optionally with an inert gas as the diluent. The ratio of the diamine compound (1) and the diol compound (2) is not particularly limited and usually 0.3–10 moles, preferably 0.5–3 moles, of the diol compound (2) per 1 mole of the diamine compound (1) is used. Preferred examples of the diluent include inert gases such as steam and nitrogen. When the diluent is used, its amount is usually 0.1–10 moles per 1 mole of the diamine compound (1).

The reaction temperature in the production of the pyrazine compound (3) is usually 250°–450° C., preferably 300°–400° C., as in the hydrogen treatment. If the reaction temperature is lower than 250° C., the conversion rates of the diamine compound (1) and the diol compound (2) as the starting materials as well as the yield of the pyrazine (3) compound are low. If the temperature exceeds 450° C., the conversion rates of the starting materials may be higher but the yield of the pyrazine compound (3) is low. The rate of feeding the mixed gas consisting of the diamine compound (1), the diol compound (2) and optional diluent to the reactor is usually 100–5,000 Hr$^{-1}$, preferably 100–3,000 Hr$^{-1}$, in space velocity (hereinafter, referred to as SV).

The silver catalyst (a) or the silver catalyst (b) may be used in combination with another catalyst (hereinafter, referred to as the catalyst A) which enables a dehydration-cyclization reaction between the diamine compound (1) and the diol compound (2) or further a partial dehydrogenation reaction of a dehydration-cyclization product in the gaseous phase. When the silver catalyst (a) or the silver catalyst (b) is used in combination with the catalyst A, a mixed gas containing usually 0.3–10 moles, preferably 0.5–3 moles, of the diol compound (2) per 1 mole of the diamine compound (1) and usually 0.1–10 moles of an optional diluent per 1 mole of the diamine compound (1) may be fed at a SV usually of 100–5,000 Hr$^{-1}$, preferably of 100–3,000 Hr$^{-1}$ to a reactor in which the silver catalyst (a) or the silver catalyst (b) is first charged and the catalyst A is charged over it. The mixed gas may be contacted with the catalyst A kept usually at 250°–450° C., preferably at 300°–400° C., to produce a dehydration-cyclization product of the diamine (1) and the diol (2) or a partial dehydrogenation product of the dehydration-cyclization product and then the reaction gas containing the products may be contacted at said SV with the silver catalyst (a) or the silver catalyst (b) kept at said reaction temperature to produce the pyrazine compound (3).

Said dehydration-cyclization product of the diamine compound (1) and the diol compound (2) means a piperazine compound of the formula:

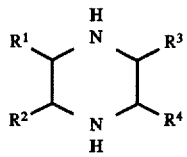

wherein $R^1$, $R^2$, $R^3$ and $R^4$ are the same as defined above, and said partial dehydrogenation product means a partial dehydration product of the above piperazine compound, or in other words, the corresponding dihydropyrazine compoud or tetrahydropyrazine compound.

The catalyst A includes the known catalysts used in the production of the pyrazine compound (3) by the catalytic reaction of the diamine compound (1) and the diol compound (2) in a gaseous phase. The preferred catalyst A is a catalyst mainly comprising zinc oxide. The expression "mainly comprising zinc oxide" means that it comprises 40% by weight or more of zinc oxide in the catalyst.

An example of a preferred embodiment for the process of the present invention is described below.

A catalyst comprising silver and at least one element selected from the group consisting of alkali metals, alkaline earth metals, zinc and lanthanoid elements carried on a carrier is charged in a reactor and the temperature in the catalyst charged area is elevated to the above described hydrogen-treating temperature, while optionally introducing a diluent to be used in the hydrogen-treating into the reactor. Thereafter, a gas comprising a hydrogen-treating agent and optional diluent are fed at the above described feeding rate to effect the hydrogen treatment.

After completion of the hydrogen treatment, the feeding of the hydrogen-treating agent is stopped and a mixed gas of the diamine compound (1), the diol compound (2) and optional diluent is contacted with the hydrogen-treated silver catalyst (a) kept at the above described reaction temperature at the above described SV to produce the pyrazine compound (3).

The production of the pyrazine compound (3) according to the present invention is carried out usually at atmospheric pressure but may be carried out under a reduced pressure or under pressurization.

The product gas containing the pyrazine compound (3) formed by the process of the present invention can be introduced to an appropriate absorbent to collect the pyrazine compound (3) and the resulting solution can be distilled to isolate the pyrazine compound (3).

EXAMPLES

The present invention will now be illustrated in more detail by means of the Examples, which should not be construed as a limitation upon the scope of the present invention.

In the Examples, rate of conversion and yield were calculated according to the following definitions.

Rate of conversion (%)=(reacted diamine compound (1) (mole)/fed diamine compound (1) (mole))×100

Yield (%)=(product (mole)/fed diamine compound (1) (mole)×100

Example 1

Preparation of a Silver Catalyst

Into a solution of 4.72 g of silver nitrate in 35 ml of deionized water was dipped 27 g of spheroidal alumina (manufactured by Sumitomo Chemical Co., Ltd., NKHO-24) to impregnate the silver nitrate solution to the spheroidal alumina. The spheroidal alumina having silver nitrate was dried at 130° C. and calcined at 450° C. for 5 hours to give a spheroidal alumina carrying silver (hereinafter, referred to as the silver catalyst 1). The silver catalyst 1 had a silver content of 10% by weight of the catalyst.

The produced silver catalyst 1 was used for a production of 2-methylpyrazine in the following process.

Production of 2-Methylpyrazine

A pyrex reactor tube having a inside diameter of 14.8 mm was packed with 23 ml of the silver catalyst 1 and the catalyst-packed portion of the tube was kept at 360° C. by heating. A mixed gas consisting of hydrogen and nitrogen (in a mixing (molar) ratio of hydrogen:nitrogen=5:3) was fed to the catalyst-packed portion at a rate of 80 ml/minute for 30 minutes to effect hydrogen treatment of the silver catalyst 1. A catalyst containing hydrogen-treated silver was obtained. After stopping the feed of hydrogen, a mixed gas of ethylene diamine, propylene glycol, water and nitrogen (in a mixing (molar) ratio of ethylene diamine: propylene glycol: water: nitrogen=1:1.2:0.93:0.7) was passed through the catalyst-packed portion at a SV of 450 Hr$^{-1}$ to perform the reaction. After an hour from the start of the reaction, the product gas was collected by absorbing in water for 10 minutes. The collected solution was analyzed by gas chromatography. The results showed that the rate of conversion was 100% and the yield of the 2-methylpyrazine was 69%.

Example 2

Preparation of Silver Catalyst

The procedure in Example 1 was repeated except that 0.94 g of lanthanum nitrate hexahydrate in addition to silver nitrate was dissolved in deionized water and the amount of spheroidal alumina was changed to 26.7 g to give a spheroidal alumina carrying silver and lanthanum oxide (hereinafter, referred to as the silver catalyst 2). The silver catalyst 2 had silver and lanthanum contents of 10% by weight and 1% by weight, respectively.

Production of 2-Methylpyrazine

The procedure in Example 1 was repeated except that the silver catalyst 1 was replaced by the silver catalyst 2 to produce 2-methylpyrazine. The rate of conversion was 100% and the yield of 2-methylpyrazine was 81%.

Example 3

Preparation of Silver Catalyst

The procedure in Example 1 was repeated except that 6.81 g of zinc nitrate hexahydrate in addition to silver nitrate was dissolved in deionized water and the amount of spheroidal alumina was changed to 25.5 g to give a spheroidal alumina carrying silver and zinc oxide (hereinafter, referred to as the silver catalyst 3). The silver catalyst 3 had silver and zinc contents of 10% by weight and 5% by weight, respectively.

Production of 2-Methylpyrazine

The procedure in Example 1 was repeated except that the silver catalyst 1 was replaced by the silver catalyst 3 to produce 2-methylpyrazine. The rate of conversion was 100% and the yield of 2-methylpyrazine was 82%.

Example 4

Preparation of Silver Catalyst

The procedure in Example 1 was repeated except that 0.94 g of lanthanum nitrate hexahydrate and 6.81 g of zinc nitrate hexahydrate in addition to silver nitrate were dissolved in deionized water and the amount of spheroidal alumina was changed to 25.2 g to give a spheroidal alumina carrying silver, lanthanum oxide and zinc oxide (hereinafter, referred to as the silver catalyst 4). The silver catalyst 4 had silver, lanthanum and zinc contents of 10% by weight, 1% by weight and 5% by weight, respectively.

Production of 2-Methylpyrazine

The procedure in Example 1 was repeated except that the silver catalyst 1 was replaced by the silver catalyst 4 to produce 2-methylpyrazine. The rate of conversion was 100% and the yield of 2-methylpyrazine was 88%.

Example 5

Preparation of Silver Catalyst

The procedure in Example 4 was repeated except that the amount of zinc nitrate hexahydrate was changed to 20.43 g and the amount of spheroidal alumina was changed to 22.2 g to give a spheroidal alumina carrying silver, lanthanum oxide and zinc oxide (hereinafter, referred to as the silver catalyst 5). The silver catalyst 5 had silver, lanthanum and zinc contents of 10% by weight, 1% by weight and 15% by weight, respectively.

Production of 2-Methylpyrazine

The procedure in Example 1 was repeated except that the silver catalyst 1 was replaced by the silver catalyst 5 to produce 2-methylpyrazine. The rate of conversion was 100% and the yield of 2-methylpyrazine was 86%.

Example 6

Preparation of Silver Catalyst

The procedure in Example 2 was repeated except that 0.94 g of lanthanum nitrate hexahydrate was replaced by 0.78 g of potassium nitrate to give a spheroidal alumina carrying silver and potassium oxide (hereinafter, referred to as the silver catalyst 6). The silver catalyst 6 had silver and potassium contents of 10% by weight and 1% by weight, respectively.

Production of 2-Methylpyrazine

The procedure in Example 1 was repeated except that the silver catalyst 1 was replaced by the silver catalyst 6 to produce 2-methylpyrazine. The rate of conversion was 100% and the yield of 2-methylpyrazine was 78%.

Example 7

Preparation of Silver Catalyst

The procedure in Example 2 was repeated except that 0.94 g of lanthanum nitrate hexahydrate was replaced by 3.16 g of magnesium nitrate hexahydrate to give a spheroidal alumina carrying silver and magnesium oxide (hereinafter, referred to as the silver catalyst 7). The silver catalyst 7 had silver and magnesium contents of 10% by weight and 1% by weight, respectively.

Production of 2-Methylpyrazine

The procedure in Example 1 was repeated except that the silver catalyst 1 was replaced by the silver catalyst 7 to produce 2-methylpyrazine. The rate of conversion was 100% and the yield of 2-methylpyrazine was 81%.

Example 8

Production of 2-Methylpyrazine

The procedure in Example 2 was repeated except that the hydrogen-treatment was not carried out to produce 2-methylpyrazine. The rate of conversion was 100% and the yield of 2-methylpyrazine was 65%.

Example 9

Production of 2-Methylpyrazine

The procedure in Example 3 was repeated except that the hydrogen-treatment was not carried out to produce 2-methylpyrazine. The rate of conversion was 100% and the yield of 2-methylpyrazine was 67%.

Example 10

Production of 2-Methylpyrazine

The procedure in Example 4 was repeated except that the hydrogen-treatment was not carried out to produce 2-methylpyrazine. The rate of conversion was 100% and the yield of 2-methylpyrazine was 73%.

Example 11

Production of 2-Methylpyrazine

The procedure in Example 5 was repeated except that the hydrogen-treatment was not carried out to produce 2-methylpyrazine. The rate of conversion was 100% and the yield of 2-methylpyrazine was 72%.

Example 12

Production of 2-Methylpyrazine

The procedure in Example 6 was repeated except that the hydrogen-treatment was not carried out to produce 2-methylpyrazine. The rate of conversion was 100% and the yield of 2-methylpyrazine was 63%.

Example 13

Production of 2-Methylpyrazine

The procedure in Example 7 was repeated except that the hydrogen-treatment was not carried out to produce 2-methylpyrazine. The rate of conversion was 100% and the yield of 2-methylpyrazine was 65%.

Comparative Example 1

Preparation of Catalyst

The procedure in Example 1 was repeated except that 4.72 g of silver nitrate was changed to 5.40 g of zinc nitrate hexahydrate and the amount of spheroidal alumina was changed to 22.8 g to give a spheroidal alumina carrying zinc oxide (hereinafter, referred to as the catalyst A1). The catalyst A1 had a zinc content of 5% by weight.

Production of 2-Methylpyrazine

The procedure in Example 1 was repeated except that the silver catalyst 1 was replaced by the silver catalyst A1 to produce 2-methylpyrazine. The rate of conversion was 94% and the yield of 2-methylpyrazine was 7%. The main product was 2-methyldihydropyrazine in a yield of 43%.

Comparative Example 2

Preparation of Catalyst

The procedure in Comparative Example 1 was repeated except that 0.75 g of lanthanum nitrate hexahydrate in addition to zinc nitrate hexahydrate was dissolved in deionized water and the amount of spheroidal alumina was changed to 22.56 g to give a spheroidal alumina carrying lanthanum oxide and zinc oxide (hereinafter, referred to as the catalyst A2). The catalyst A2 had lanthanum and zinc contents of 1% by weight and 5% by weight, respectively.

Production of 2-Methylpyrazine

The procedure in Example 1 was repeated except that the silver catalyst 1 was replaced by the silver catalyst A2 to produce 2-methylpyrazine. The rate of conversion was 95% and the yield of 2-methylpyrazine was 7%. The yield of 2-methyldihydropyrazine was 44%.

Example 14

Production of 2-Ethylpyrazine

The procedure in Example 2 was repeated except that ethylene diamine was replaced by 1,2-diaminobutane, propylene glycol was replaced by ethylene glycol, water was not used and the mixing (molar) ratio of the mixed gas was changed to 1,2-diaminobutane:ethylene glycol:nitrogen= 1:1.2:0.7 to produce 2-ethylpyrazine. The rate of conversion was 100% and the yield of 2-ethylpyrazine was 69%.

Example 15

Production of 2,3-Dimethylpyrazine

The procedure in Example 2 was repeated except that propylene glycol was replaced by 2,3-butanediol, water was not used and the mixing (molar) ratio of the mixed gas was changed to ethylene diamine: 2,3-butanediol:nitrogen= 1:1.2:0.7 to produce 2,3-dimethylpyrazine. The rate of conversion was 100% and the yield of 2,3-dimethylpyrazine was 72%.

What is claimed is:

1. A process for producing a pyrazine compound of the general formula (3):

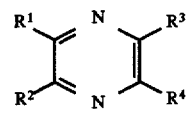
(3)

wherein $R^1$, $R^2$, $R^3$ and $R^4$, which are the same or different from each other, represent a hydrogen atom or a lower alkyl group, which comprises catalytically reacting in a gaseous phase a diamine compound of the formula (1):

(1)

wherein $R^1$ and $R^2$ are the same as defined above, with a diol compound of the formula (2):

(2)

wherein $R^3$ and $R^4$ are the same as defined above, in the presence of a catalyst containing hydrogen-treated silver.

2. The process according to claim 1, in which the catalyst containing hydrogen-treated silver is a catalyst having a hydrogen-treated silver carried on at least one carrier selected from the group consisting of alumina, zirconia and silicon carbide.

3. The process according to claim 1, in which the catalyst containing hydrogen-treated silver further contains at least one element selected from the group consisting of alkali metals, alkaline earth metals, zinc and lanthanoid elements.

4. A process for producing a pyrazine compound of the formula (3):

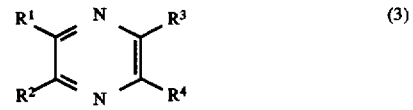
(3)

wherein $R^1$, $R^2$, $R^3$ and $R^4$, which are the same or different from each other, represent a hydrogen atom or a lower alkyl group, which comprises catalytically reacting in a gaseous phase a diamine compound of the formula (1):

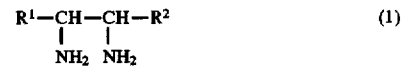
(1)

wherein $R^1$ and $R^2$ are the same as defined above, with a diol compound of the formula (2):

(2)

wherein $R^3$ and $R^4$ are the same as defined above, in the presence of a catalyst containing silver and at least one element selected from the group consisting of alkali metals, alkaline earth metals, zinc and lanthanoid elements.

5. The process according to claim 4, in which the silver and at least one element selected from the group consisting of alkali metals, alkaline earth metals, zinc and lanthanoid elements are carried on at least one carrier selected from the group consisting of alumina, zirconia and silicon carbide.

6. The process according to claim 2, in which the catalyst containing hydrogen-treated silver further contains at least one element selected from the group consisting of alkali metals, alkaline earth metals, zinc and lanthanoid elements.

* * * * *